US009161721B2

(12) United States Patent
Yang

(10) Patent No.: US 9,161,721 B2
(45) Date of Patent: *Oct. 20, 2015

(54) ELECTRONIC DEVICE AND METHOD OF USING THE SAME

(76) Inventor: Chang-Ming Yang, Jhunan Township (TW)

(*) Notice: Subject to any disclaimer, the term of this patent is extended or adjusted under 35 U.S.C. 154(b) by 356 days.

This patent is subject to a terminal disclaimer.

(21) Appl. No.: 13/487,655

(22) Filed: Jun. 4, 2012

(65) Prior Publication Data
US 2012/0238845 A1 Sep. 20, 2012

Related U.S. Application Data

(63) Continuation-in-part of application No. 12/053,553, filed on Mar. 22, 2008, now Pat. No. 8,193,465, which is a continuation-in-part of application No. PCT/CN2005/001520, filed on Sep. 21, 2005.

(51) Int. Cl.
H01H 13/702 (2006.01)
A61B 5/00 (2006.01)
H01H 3/14 (2006.01)
A61B 5/024 (2006.01)

(52) U.S. Cl.
CPC .............. A61B 5/6805 (2013.01); A61B 5/6804 (2013.01); H01H 3/14 (2013.01); A61B 5/0002 (2013.01); A61B 5/024 (2013.01); H01H 13/702 (2013.01); H01H 2203/0085 (2013.01)

(58) Field of Classification Search
CPC .. H01H 2239/078; H01H 3/141; H01H 3/142
USPC ........................................................ 200/512
See application file for complete search history.

(56) References Cited

U.S. PATENT DOCUMENTS

| | | | | |
|---|---|---|---|---|
| 5,986,221 A * | 11/1999 | Stanley | .......................... | 177/136 |
| 6,600,120 B1 * | 7/2003 | Marmaropoulos et al. | ... | 200/515 |
| 6,696,653 B1 * | 2/2004 | Smith et al. | ................. | 200/85 R |
| 8,193,465 B2 * | 6/2012 | Yang et al. | ..................... | 200/512 |
| 2005/0156486 A1 * | 7/2005 | Orten | ............................ | 310/322 |

* cited by examiner

Primary Examiner — Renee S Luebke
Assistant Examiner — Ahmed Saeed
(74) Attorney, Agent, or Firm — Osha Liang LLP

(57) ABSTRACT

An electronic device includes an upper layer made of a non-conductive material; a lower layer made of a non-conductive material, wherein at least one of the upper layer and the lower layer is made of a resilient material having a sufficient elasticity such that it will return to an original shape after being deformed, wherein the upper layer comprises an upper conductor and the lower layer comprises a lower conductor and a space is provided between the upper conductor and the lower conductor such that the upper conductor and the lower conductor are not in contact until a force is applied to deform at least one of the upper layer and the lower layer. A sensor device for human body testing connected with the lower conductor, or the lower conductor is configured to function as part of a sensor device for human body testing.

17 Claims, 9 Drawing Sheets

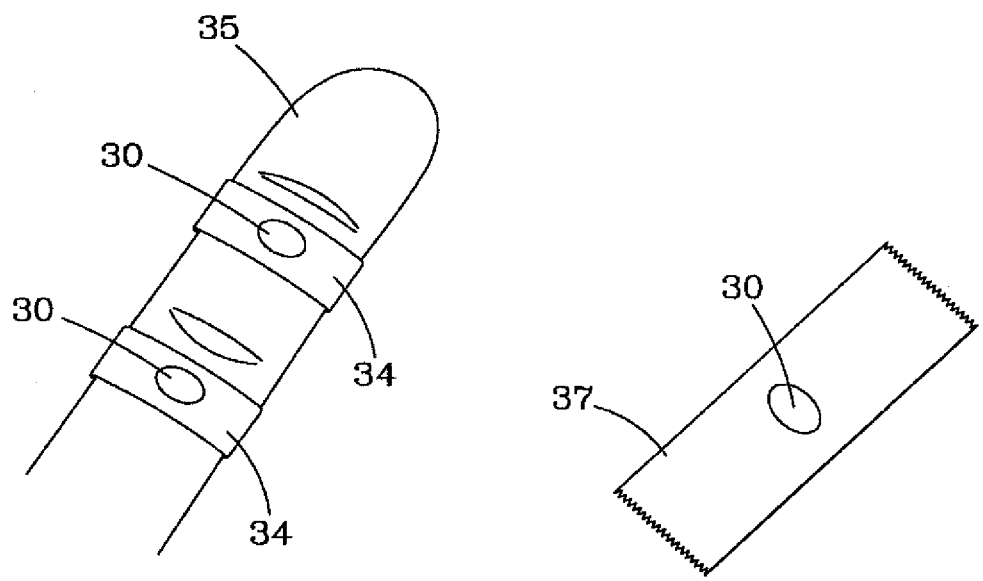
FIG. 6
FIG. 7
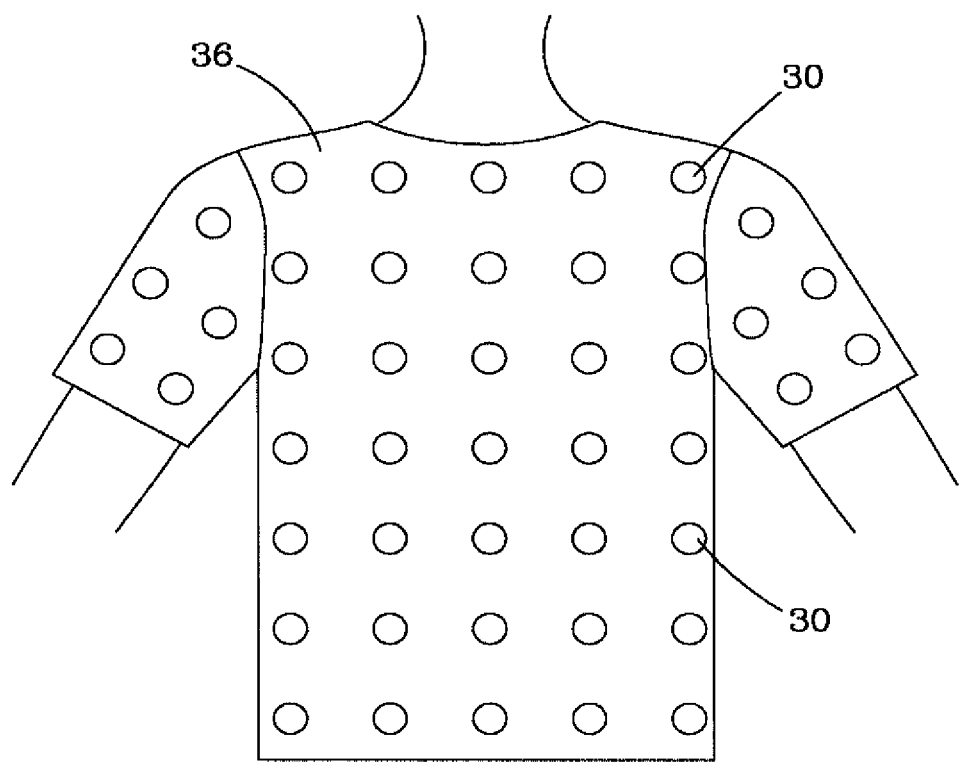
FIG. 8

ELECTRONIC DEVICE AND METHOD OF USING THE SAME

CROSS REFERENCE TO RELATED APPLICATIONS

This application is a continuation-in-part application of application Ser. No. 12/053,553, filed on Mar. 22, 2008, which is a continuation-in-part of International patent application Ser. No. PCT/CN2005/001520, filed on Sep. 21, 2005. This application claims the benefits of these prior applications and incorporates the disclosures of these prior applications by reference in their entireties.

FIELD OF THE INVENTION

This invention relates to human body testing/monitoring, especially relates to devices designed to be carried around, and can test any of the following: breath sounds, heart rate, EKG, body fat, sweat wetness, $O_2$ saturation, pulse rate, blood pressure, body temperature, urine sugar, or change in pressure at a point where pressure is applied.

BACKGROUND

Well-known electronic devices have been widely used for human body testing purposes, for example, electronic thermometers, electronic blood pressure monitors, lung sound-sensing and heart rhythm-sensing devices. Yet, the aforementioned devices have 3 common disadvantages: (1) the aforementioned devices are all external devices that are inconvenient to be carried around; (2) the aforementioned devices are all operated by an on-off switch, to be switched on before use and turned off immediately after. When repetitive and short-time monitoring is needed, as in mountain-climbing, wherein what is actually needed is to take the heart rate every 5 minutes for a duration of 10 seconds, turning the switch on and off repetitively is cumbersome; and (3) in the process of using the aforementioned devices, the user needs to turn on the switch, and then apply pressure on the devices so that it presses on the part to be monitored or tested. For a patient or a busy operator, this is very inconvenient.

SUMMARY OF INVENTION

In one aspect, this invention relates to an electronic device that can be fixed to an article worn by a user, for example clothes, pants, hats, gloves, ties, socks, scarves, etc., so it can be carried around conveniently. Embodiments of the invention relate to electronic devices, the on-off switches of which are designed to be easy to use in repetitive, short-time monitoring or testing fashion. Some embodiments of the invention relate to electronic devices that integrate the actions of switching on and applying pressure on the part to be tested or monitored into one single action, thereby proving ease of use.

An embodiment of the invention relates to electronic devices and methods that may include: an upper piece (which may be a resilient piece in some embodiments), and a base plate (or lower piece). The upper piece may include an upper conductor; the base plate may be connected to the upper piece, with a space between the upper piece and the base plate. The base plate is designed with a lower conductor, which is separated from the upper conductor with a space or crevice. An optional electric power source is connected to the upper conductor and the lower conductor electrically. Note that the upper and lower are used herein to denote different parts in an electronic device for illustration purpose only; they are not intended to indicate the physical up and down directions/locations.

One aspect of the present invention is directed to an electronic device comprising: an upper piece (which may be a resilient piece), made of a non-conductive (or a resilient material) that is sufficiently elastic to cause an upper conductor, which is on the upper piece and electrically conductive, to return to an original position after depression; a base plate made of a non-conductive material, wherein a space is provided between the resilient piece and the base plate, the base plate having a lower conductor and a side at which the lower conductor can contact the upper conductor; a non-conductive material, which is located between the upper piece and the base plate; the upper piece responsive to an applied force by deforming so that the upper conductor and the lower conductor contact each other to switch a circuit on; and removal of the applied force causing the upper piece and base plate to separate to switch the circuit off; and one or more tape, ring, clothing or apparel attachment sites around a periphery of the resilient piece for direct setting within a piece of tape, a ring, or a piece of clothing or apparel.

Another embodiment also includes adhesive tape which is located on the base plate and is used to stick the electronic device onto a body joint or around a user's eyes.

In yet another embodiment, the upper (or resilient) piece has varying thickness or different moduli of elasticity according to a desired sensitivity of the electronic device.

In yet another embodiment, the upper piece is made of a non resilient material and the base plate is made of a resilient material.

In yet another embodiment, the upper piece and the base plate use the same resilient material.

In yet another embodiment, the sensor device may be connected with an electronic source. The sensor device may be used to test breath sounds, heart rhythm, EKG, body fat, sweat wetness, $O_2$ saturation, pulse rate, blood pressure, body temperature, pressure or urine sugar.

In yet another embodiment, a upper piece may be joined between the sensor device and the base plate.

In yet another embodiment, the sensor device electrically connects to a wireless transmission interface for transmitting wirelessly to the outside world test results of the sensor device, and receiving information from the outside world.

In yet another embodiment, the sensor device electrically connects to a monitor or a speech sound installation.

In yet another embodiment, the sensor device electrically connects to a processor having a threshold time setting, in which force upon the device for more than a set time is stored, displayed or transmitted.

In yet another embodiment, at least one flexible blade, which is located between the upper (resilient) piece and the base plate, has a fixed end located between the resilient piece and the base plate, and a free end located between the upper conducting plate and the lower conducting plate; the flexible blade being made of non-conductive material.

In yet another embodiment, a separated lamina is electrically conductive and connected to an electronic source, said separated lamina being fixed between the base plate and the resilient piece; and a space is provided between it and each of the upper conductor and the lower conductor.

In yet another embodiment, a microphone connected with an electronic source.

In yet another embodiment, a ring which is mounted on the base plate, and configured to be worn on a joint and set on a vehicle's steering wheel.

In yet another embodiment, there is clothing to which the base plate is fixed.

In yet another embodiment, clothing is fixed between the upper (or resilient) piece and base plate.

In yet another embodiment, the electronic device is placed between the fibers of the clothing.

In yet another embodiment, an area on the clothing where the resilient piece is located contains at least a type of functional diagram.

In yet another embodiment, a functional diagram can be made by dyeing or stitching.

In yet another embodiment, the electronic device is one of several electronic devices arranged in an array.

Another aspect of the present invention is directed to an electronic device comprising: a resilient piece, made of non-conductive and resilient material that is sufficiently elastic to cause an upper conductor, which is electrically conductive, to return to an original position after depression; a base plate made of non-conductive material, a space being provided between the resilient piece and the base plate, the base plate having a lower conductor that is electrically conductive and a side at which the lower conductor can contact the upper conductor; the resilient piece responsive to an applied force by deforming so that the upper conductor and the lower conductor contact each other to switch a circuit on; and removal of the applied force causing the resilient piece and base plate to separate to switch the circuit off; a sensor device mounted on an opposite side of the base plate from the side of the base plate at which the lower conductor and upper conductor contact; and one or more tape, ring, clothing or apparel attachment sites surround the resilient piece for direct setting within a piece of tape, a ring, or a piece of clothing or apparel.

In yet another aspect, the sensor device is connected with an electronic source and is used to test breath sounds, heart rhythm, EKG, body fat, sweat wetness, O2 saturation, pulse rate, blood pressure, body temperature, pressure or urine sugar; a resilient piece is joined between the sensor device and the base plate; the sensor device electrically connects to a wireless transmission interface for transmitting wirelessly to the outside world test results of the sensor device, and receiving information from the outside world; the sensor device electrically connects to a processor having a threshold time setting, in which force upon the device for more than a set time is stored, displayed or transmitted; and either: (1) at least one flexible blade, which is located between the resilient piece and the base plate, has a fixed end located between the resilient piece and the base plate, and a free end located between the upper conducting plate and the lower conducting plate; the flexible blade being made of non-conductive material; or (2) a separated lamina that is electrically conductive and connected to an electronic source, said separated lamina being fixed between the base plate and the resilient piece; and a space is provided between it and each of the upper conductor and the lower conductor. In yet another aspect, the present invention is directed to an electronic device comprising: a plate-shaped upper conducting plate, which is electrically conductive; a plate-shaped lower conducting plate, which is electrically conductive; and a non-conductive material, located between the upper conducting plate and the lower conducting plate so that a space is provided between the upper conducting plate and the lower conducting plate, and the upper and lower conducting plates operatively contacting each other at one or more points.

Yet another embodiment includes a sensor device mounted on an opposite side of the lower contacting plate from the one or more points of the lower conductor and upper conductor contact.

Yet another aspect of the present invention is a method of using any of the various possible combinations of embodiments shown herein below and above.

BRIEF DESCRIPTION OF THE DRAWINGS

With the following detailed description and illustrations shown in the drawings, one can understand more accurately the make-up and special features of electronic devices of the invention.

FIG. 6 shows a schematic diagram of the electronic device's third example embodiment in actual use on the finger;

FIG. 7 shows a schematic diagram of the electronic device's third example embodiment in actual use on the adhesive tape;

FIG. 8 shows a schematic diagram of the electronic device's third example embodiment in actual use on the clothing;

EXPLANATION OF THE MAIN PARTS WITH LABELS IN THE ILLUSTRATIONS

Figure 1:
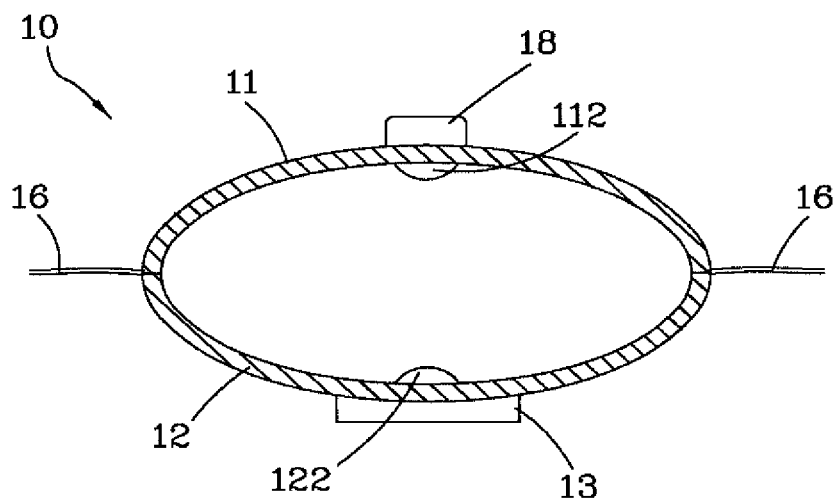
FIG. 1 shows a cut-away view of a first example embodiment of an electronic device of the present invention.

Electronic 11 resilient piece 112 Upper conductor device 10 12 Base plate 122 Lower conductor 13 Sensor device 14 Monitor 15 Transmission interface 16 Tested subject's coat 17 Illustration of functions 18 Microphone 19 Processor Electronic 21 Resilient piece 212 Upper conductor device 20 213 Hole 22 Base plate 222 Lower conductor 223 Hole 23 Sensor device 24 Spring 25 Tested subject's shirt 26 Tested subject's skin Electronic 31 Upper conducting plate 32 Lower conducting plate device 30 33 Non-conductive material 34 Cover ring 35 Finger 36 Clothes 37 Adhesive tape Electronic 41 Resilient piece 412 Upper conductor device 40 413 Hole 42 Base plate 422 Lower conductor 423 Hole 43 Blade 44 Sensor device Electronic 51 Resilient piece 512 Upper conductor device 50 513 Hole 52 Base plate 522 Lower conductor 523 Hole 53 Non-conductive material 54 Blade 55 Sensor device Electronic 61 Resilient piece 612 Upper conductor device 60 62 Base plate 622 Lower conductor 63 Separated lamina 64 Sensor device Electronic 71 Upper conducting plate 72 Lower conducting plate device 70 73 Non-conductive material 74 Separated lamina 75 Sensor device Specific Implementing Pattern:

One aspect of the present invention is directed to an electronic device. In the following reference FIGS. 1 through 3, this invention's first example embodiment of the electronic device 10 includes resilient piece 11, base plate 12, sensor device 13, processor 19, monitor 14, transmission interface 15 and electronic source (not shown). Among which, the resilient (or upper) piece 11 is like a dome shape, it is facing down, and is made of resilient, non-conductive material. Applying pressure downwards will cause the resilient piece 11 to deform. Removal of the applied force allows the resilient piece 11 to return to its prior shape. The upper conductor 112 is located on the central portion of the lower surface of the resilient piece 11. The base plate 12 is like a dome shape, and is made of non-conductive material. The dome shape base plate utilizes a disc-to-disc linkage located below the resilient piece 11. There is a space between the resilient piece 11 and the base plate 12. The lower conductor 122 is located on the central portion of the upper surface of the base plate. There is a gap between the lower conductor 122 and the upper conductor 112. The sensor device 13 is located at the lower surface of the base plate 12, and is electrically-connected to the lower conductor 122.

Based on this example embodiment, the sensor device 13 is a heart rhythm sensor device which can be used to monitor heart rhythm and subsequently transmit the results to the processor 19. For example, setting the threshold value in the processor at 3 seconds. If the resilient piece 11 is pressed for only 2 seconds, then the processor will ignore and delete the results of this test since it is below the threshold value set in the processor. In other words, if the sensor device is pressed for more than 3 seconds, then the results of this test will be shown on the monitor 14; or the results can be sent wirelessly via the transmission interface 15 to the outside world. From here, we can ignore the irrelevant data from tests that are done in too short a time, thereby preventing sensing by mistake. The electronic source provides the needed power to the sensor device 13, monitor 14 and the transmission interface 15, and is electrically connected to the upper conductor 112 and the lower conductor 122.

Figure 2:
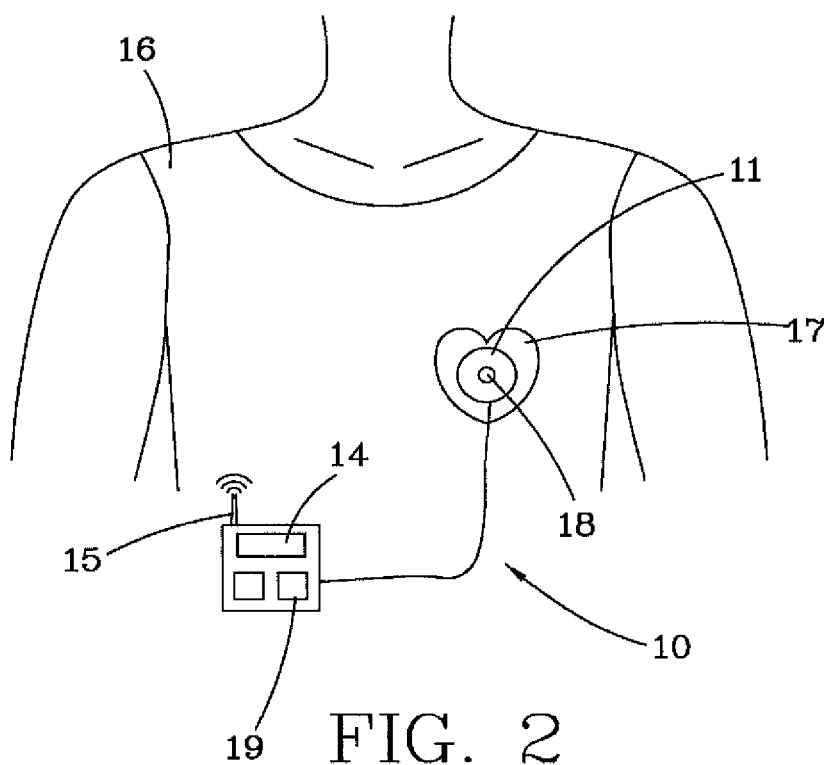
FIG. 2 shows a schematic diagram of this first example embodiment in actual use.
Figure 3:
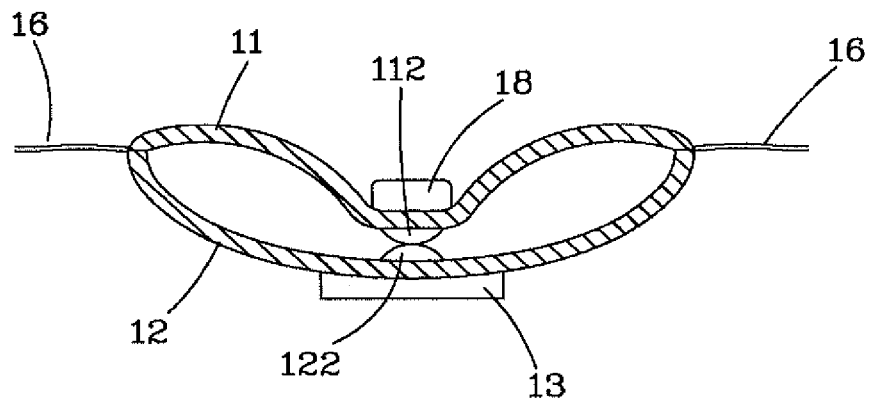
FIG. 3 shows a schematic diagram of the electronic device in FIG. 1 in actual use.

As shown in FIG. 2, the electronic device 10 is directly fixed to the subject's coat 16. As shown in FIG. 1, the coat 16 is fixed between the base plate 12 and resilient piece 11, causing the sensor device 13 to come into direct contact with the part to be sensed, as in the subject's left chest which is closest to the heart. As shown in FIG. 3, during sensing, the subject only needs to apply light pressure on the resilient piece 11, causing it to be deformed, which then causes the upper conductor 112 and the lower conductor 122 to come in direct contact with each other, completing the electrical circuit. When the sensor device 13 is activated, it starts to sense and monitor the subject's heart rhythm, and through the processor 19 which can decide whether sensing time reaches the threshold 3 seconds or not. If it does, then the results are shown on the monitor 14, or be transmitted wirelessly to the outside world through the transmission interface 15. On the coat 16, a functional diagram 17 where the functions of the electronic device 10 is indicated, and the functional diagram 17 can be dyed or stitched on the resilient piece 11. For example, in this applied example where the sensor device 13 is a heart rhythm sensor, the functional diagram 17 can be in the shape of a heart.

Since this electronic device 10 is directly set to the subject's coat 16, it does away with the inconvenience of carrying a sensor device. And during sensing, the subject needs only to press on the resilient piece with one hand, and he turns the switch on and simultaneously causes the sensor device 13 to come in contact with the site to be sensed. Because of this, even repetitive and short-interval testing, it seems very convenient. Also, as the circuit is only powered on when resilient piece 11 is pressed, otherwise the circuit is always open. It decreases the energy consumption and is good for the green technology. Aside from this, this electronic device is also provided with an anti-false sensing feature. In addition, this invention's electronic device improves on the disadvantages of similar devices in the market, thereby achieving its goal of our invention.

Moreover, there are several variations to this electronic device 10. For example, the locations of the resilient piece 11 and the base plate 12 can be interchanged. And the elastic base plate 12 is placed on top of the elastic piece 11. Or, both the resilient piece 11 and the base plate 12 use the same resilient material. All these changes give the same results. Secondly, there is a different thickness or different modulus of elasticity of the resilient piece that can change the sensitivity of the electronic device 10. Because of this, during design, we can choose materials of different sensitivity to be used for the resilient piece based on the practical demands for the sensitivity of the electronic device 10. Several exemplary resilient piece materials include chloroprene rubber (CR) (such as in wetsuits and related water accessories); styrene butadiene rubber (SBR) (for cell phone cases, coolers and the like); a 30%:70% ratio of CR to SBR for sports suits, medical supports, and the like; silicone rubber; nylon; polyester; polypropylene; polyurethane; and sponge. However, any material suitable for providing a resilient and sufficiently elastic construction can be used.

Furthermore, we can use other types of sensor device instead of the above-mentioned sensor device 13, as in those used in sensing lung sound, pulse rate, blood pressure, body temperature, urine sugar, body fat, sweating, ECG, O2 saturation, or pressure sensors. We can also vary the detected portion of the body, change the functional diagram 17 and reset the threshold value in the processor 19 based on the monitor factors. For example, we can use a body temperature sensor device 13 and place it under the armpit, set a longer threshold value of time (for example, 1 minute), for it to have enough time to achieve heat equilibrium. As regards the sensor device for urine sugar, we can place the sensor device near a perineum of a diaper, or dye or stitch a functional diagram, or freely adjust any aspect based on real demands.

In addition, the processor 19 can be equipped with a function to turn the sensor device on and off, change the sensor device's 13 sense time, sense frequency, and sense mode or other parameters based on the user's needs. Or these settings can be set to be activated based on the duration of time the user presses on the resilient piece 11, if it crosses the threshold value set in the processor 19, thereby preventing activation by accidental-touching. Moreover, the transmission interface 15 can be used to receive remote signals for the purpose of remote activation and inactivation of the sensor device, or to change the procedure of the test parameters. Regarding the monitor 14, it can be a cellular phone, PDA or a computer that shows the test results. Also, a light-emitting body can be used to emit a warning sign to the people around (such as in the form of a "red cross" or the number '119") whenever the sensor device 13 senses an abnormal result, such as an overly-high blood pressure or sudden stop of the heartbeat. Or, signals can be sent via the transmission interface 15 to relatives far away, or directly call an ambulance. And also, the electronic device 10 can be equipped with a microphone 18 in the resilient piece 11 and connected electrically with the upper conductor 112, to allow the user to directly communicate with or seek help from the outside world via the transmission interface 15. The place where the resilient piece 11 is located on the coat 16 can be printed with a functional diagram 17 to differentiate between emergency articles and communication articles. Included in the functional diagram 17 are illustrations of the red cross, ambulance and relatives.

Aside from these, when the electronic device 10 is designed to be an EKG or blood pressure sensor, the time needed for testing needs to be at least 1-2 minutes. Because of this, the subject's coat 16 can be equipped with a self-inflatable airbag. When the subject presses on the resilient piece 11, the upper conductor 112 comes into contact with the lower conductor 122, causing the inflatable bag to self-inflate and thereby pressing the sensor device 13 against the skin of the part to be tested. Or the subject's shirt can be designed to be tight-fitting, which can lessen inconvenience on the subject who needs to maintain a proper position. This increases the ease of use.

Figure 4:
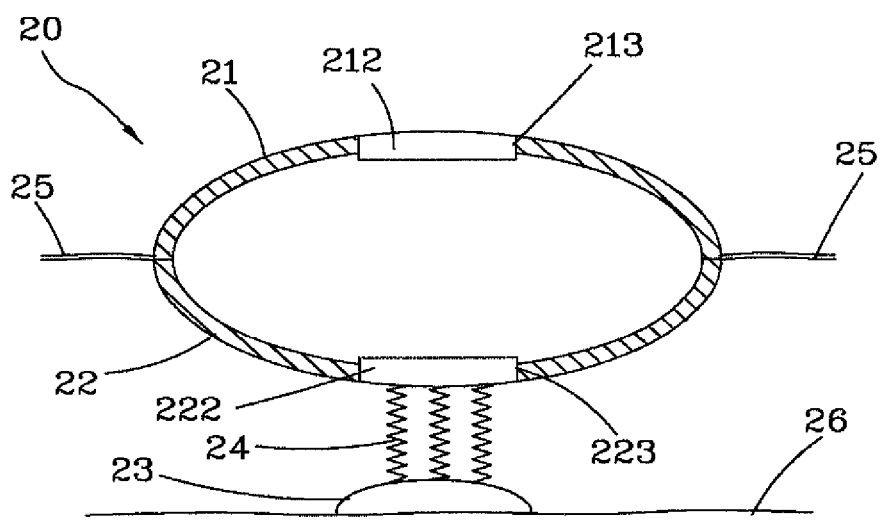
FIG. 4 shows a cut-away view of a second example embodiment of an electronic device of the present invention.
Figure 5:
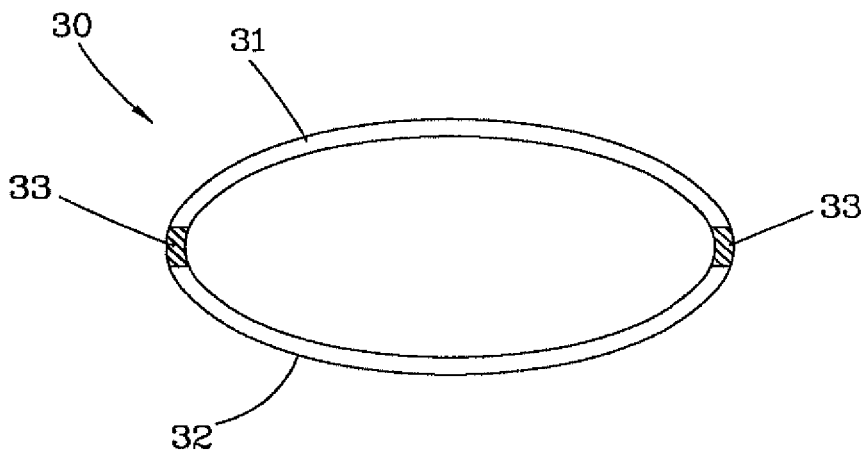
FIG. 5 shows a cut-away view of a third example embodiment of an electronic device of the present invention.

As shown in FIG. 4, this invention's second example embodiment of the electronic device 20 includes a resilient piece 21, base plate 22, sensor device 23, 3-row spring 24, monitor (not shown), and electronic source (not shown). Among which, the resilient piece 21 is like a dome shape and made of resilient, non-conductive material. In the disk center of the resilient piece 21, the upper conductor 212 and a hole 213 are located, where the upper conductor 212 is mounted. The base plate 22 is also like a dome shape, is made of resilient, non-conductive material, and is connected to the resilient piece between which there is a space. In the disk center of the base plate 22, the lower conductor 222 and an hole 223 are located, where the lower conductor 222 is mounted. There is a crevice between the lower conductor 222 and the upper conductor 212. The applied example of the sensor device 23 is a lung sound sensor, which is electrically connected to the lower conductor 222. This sensor device 23 is used to test human lung sound, and shows the test results on the monitor. The 3-combined spring 24 and the sensor device 23 and the base plate 22 are joined together. The electronic source provides the needed power to the sensor device 23 and the monitor, and is electrically connected to the upper conductor 212 and the lower conductor 222.

Fixing the electronic device 20 directly on the subject's shirt 25, so that the sensor device 23 is pressing down directly on the part to be tested 26. During testing, press lightly on the resilient piece 21 to promote contact between the upper conductor 212 and the lower conductor 222, thereby the electrical circuit is on. As the sensor device 23 is activated, it starts to test the subject's lung sound. Utilizing this type of structure, even if the subject performs extreme exercise, thereby deviating the position of the resilient piece 21 and the base plate 22 from the area to be tested, the sensor device 23 can still remain fixed to the site to be tested. For this reason, not only can the electronic device 20 maintain its active test status at all times, but it also can not be affected by the subject doing exercise and thereby moving the sensor device 23 from the tested site 26, causing error. The electronic device 20 can also be carried around conveniently, and be operated by one hand even during repetitive, short-interval testing. This is extremely convenient.

Referring to FIGS. 5 through 8, this invention's third example embodiment of the electronic device 30 includes an upper conducting plate 31, lower conducting plate 32, non-conductive material 33, processor (not shown), monitor (not shown), and electronic source (not shown). Among which, the upper conducting plate 31 and the lower conducting plate 32 is like a dome shape and are made of resilient conductive material. The non-conductive material 33 is ring-shaped. The edges of the disks of the upper conducting plate 31 and the lower conducting plate 32 are fixed separately to the upper and lower edges of the non-conductive material 33. The upper conducting plate 31 and lower conducting plate 32 are separated from the non-conductive material to form a space. The processor is electrically connected to the upper conducting plate 31 and the lower conducting plate 32 separately. It can distinguish whether the circuit is on or off between the upper conducting plate 31 and the lower conducting plate 32, and can process this mutual electrical conductance signal and show it on the monitor. The electronic source provides the power needed for the processor and the monitor, and is electrically connected to the upper conducting plate 31 and the lower conducting plate 32.

The electronic device 30 is installed to the ring 34 to be put on the subject's finger 35 near the joint. This can be used in deaf-mute persons as a means of communicating with each other, similarly among medical personnel in the operating room. If the subject wishes to express a personal opinion, he only needs to bend his finger, forcing the upper conducting plate 31 and the lower conducting plate 32 to change shape, thereby coming into contact with each other, completing an electrical circuit. Afterward, when the processor receives this electrical conducted signal, it processes it and shows it on the monitor. For example, it can be designed in such a way that bending the finger once means "Yes", and twice means "No", or three times or more or at different intervals to mean other different words, based on the needs of the user. Moreover, the monitor can be equipped with speakers, which can directly broadcast the user's opinion in spoken language for others to hear. Another thing is, as shown in FIG. 7, we can use the adhesive tape 37 to fix the electronic device 30 on the eyelids, hence allowing a special group of patients (quadriplegics) to express their thoughts through blinking.

Besides, this invention's third example embodiment of the electronic device 30 can have other uses. For example, we can have several electronic devices 30 placed on the wrist joints, elbow joints, or the knee joints, and sharing a common processor to process different signals as a whole. Utilizing this arrangement, the electronic device 30 can be used as an exercise-assist equipment, helping beginners learn essential actions, just like learning to play golf, where the different electronic devices 30 on the different joints will help us determine if the user's posture is correct, and showing it on the monitor. It can even show clearly the position of the incorrect posture, hence improving the user's learning results.

Again as shown in FIG. 8, we can use several electronic devices 30 and arrange them in matrix form, and placing them between the fibers of the clothes 36 of critically ill, vegetative and chronically bed-ridden patients to wear. With the help of the test results, we can promptly know the condition of body areas that are pressured under prolonged time in these patients, and can alert nurses in advance to help the patients, thereby preventing bedsores or eczema. Moreover, we can install the electronic device 30 to a ring placed on the steering wheel as a tool to assist drivers. In this case, the electronic device will be used to test if the driver is grasping the steering wheel correctly. If not, the monitor will immediately show a warning signal to alert the driver, thereby preventing accidents.

Figure 9:
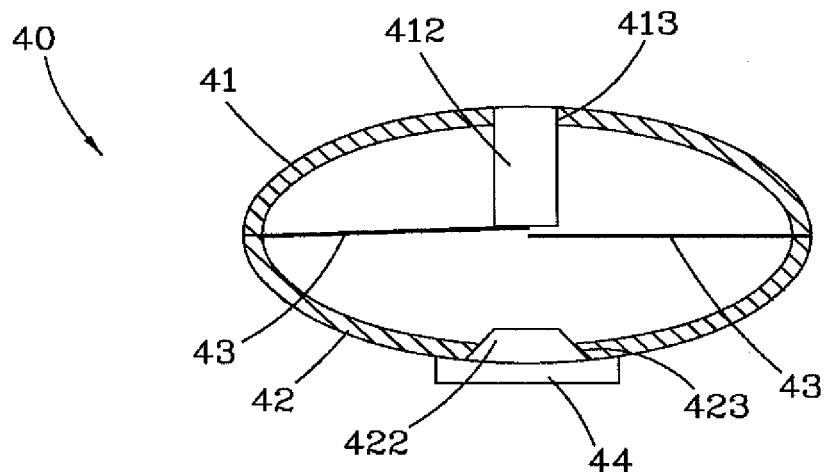
FIG. 9 shows a cut-away view of a fourth example embodiment of an electronic device of the present invention.
Figure 10:
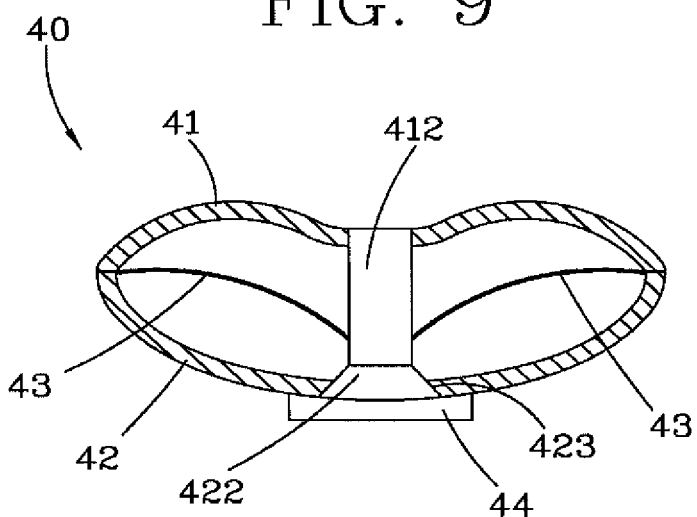
FIG. 10 shows a schematic diagram of the electronic device in FIG. 9 in actual use.

As shown in FIGS. 9 through 10, this invention's fourth example embodiment of the electronic device 40 includes a resilient piece 41, base plate 42, two blades 43, sensor device 44, monitor (not shown), and electronic source (not shown). Among which, the resilient piece 41 forms a dome shape and made of resilient, non-conductive material. In the disk center of the resilient piece 41, the upper conductor 412 and a hole 413 are located, where the upper conductor 412 is mounted. The base plate 42 is also dome-shaped, is made of resilient, non-conductive material, and is connected to the resilient piece 41, between which there is a space. In the disk center of the base plate 42, the lower conductor 422 and a hole 423 are located, where the lower conductor 422 is mounted. The two blades 43 are each rectangular, board-like plates, and are flexible, non-conductive material. Its fixed end is fixed on the spot where the elastic piece 41 and the base plate 42 are joined, while its free end is located between the upper conductor 412 and the lower conductor 422. The distance between the two blades 43 and the upper conductor 412 is smaller than the distance between the two blades 43 and the lower conductor 422. The sensor device 44 is located on the lower surface of the base plate 42, and is electrically connected to the lower conductor 422. The sensor device is used to test the subject's physiological status, and the results are shown on the monitor. The electronic source provides the needed power to the sensor device 44 and the monitor, and is electrically connected to the upper conductor 412 and the lower conductor 422.

When the electronic device 40 is fixed to the subject's garment, he only needs to press lightly on the resilient piece 41, causing it to deform and change shape, leading to the upper conductor 412 pushing apart the two blades 43 and coming into contact with the lower conductor 422, completing the electrical circuit on, as shown in FIG. 10. When the sensor device 44 is activated, it starts to test. If the subject is in the process of moving, and unintentionally pulls tightly his shirt where the electronic device 40 is located, this will impel the base plate 42 to change shape. The lower conductor 422 will not be able to come into contact with the upper conductor 412 because it is separated by the two blades 43. Hence, this will prevent testing by mistake and power wastage. Based on this, the electronic device 40 not only allows the subject to be tested at any time based on his needs, but also can prevent testing by mistake due to the subject's exaggerated movements.

Figure 11:
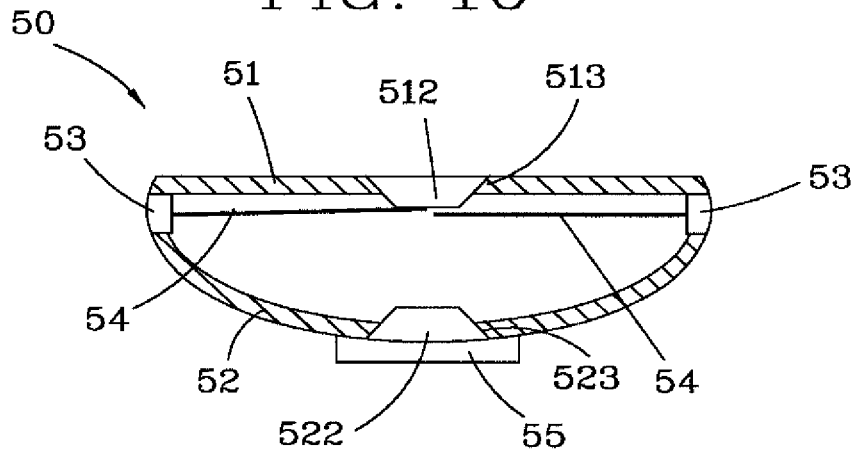
FIG. 11 shows a cut-away view of a fifth example embodiment of an electronic device of the present invention.

As shown in FIG. 11, this invention's fifth example embodiment of the electronic device 50 includes a resilient piece 51, base plate 52, non-conductive material 53, two blades 54, sensor device 55, monitor (not shown), and electronic source (not shown). Among which, the resilient piece 51 is round, lamina-shaped and made of resilient non-conductive material. In the center of the resilient piece 51 are the upper conductor 512 and an opening 513 where the upper conductor 512 is mounted. The base plate 52 is like a dome shape and is made of resilient non-conductive material. In the disk center are located the lower conductor 522 and a hole 523 where the lower conductor 522 is mounted. The non-conductive material 53 is ring-shaped. The resilient piece 51 and the base plate 52 are fixed on the upper and lower edges of the non-conductive material 53 respectively. There is a space between the upper conductor 512, the lower conductor 522 and the non-conductive material 53. The two blades 54 are each rectangular, board-like plates, and are flexible, non-conductive material. Its fixed end is fixed on the non-conductive material 53, while its free end is located between the upper conductor 512 and the lower conductor 522. The distance between the two blades 54 and the upper conductor 512 is smaller than the distance between the two blades 54 and the lower conductor 522. The sensor device 55 is located on the lower surface of the base plate 52, and is electrically connected to the lower conductor 522. The sensor device is used to test the subject's physiological status, and the results are shown on the monitor. The electronic source provides the needed power to the sensor device 55 and the monitor, and is electrically connected to the upper conductor 512 and the lower conductor 522.

This application example has a similar effect as the fourth application example. The user simply has to press on the resilient piece 51, causing the upper conductor 512 to change the shape of the two blades 54, thereby coming into contact to the lower conductor 522 it is on. On the other hand, if the user mistakingly presses on the base plate 52, the lower conductor 522 will be obstructed by the two blades 54, preventing electrical connection with the upper conductor 512.

Figure 12:
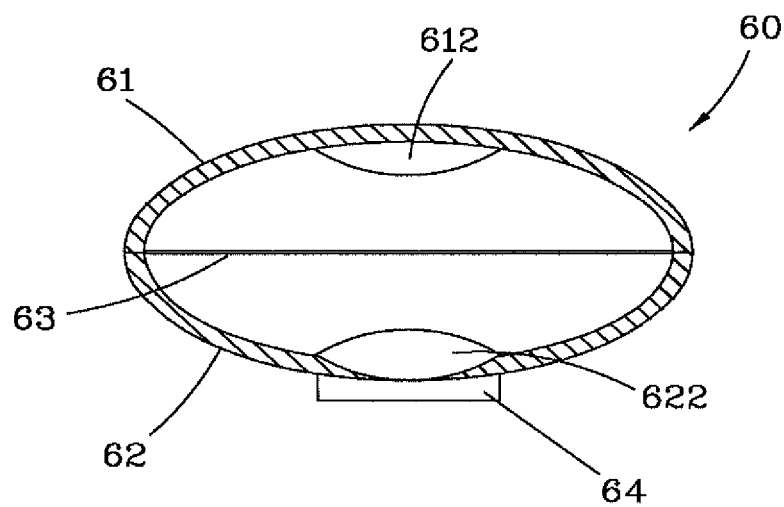
FIG. 12 shows a cut-away view of a sixth example embodiment of an electronic device of the present invention.

Referring to FIG. 12, this invention's sixth example embodiment of the electronic device 60 includes a resilient piece 61, base plate 62, separated lamina 63, sensor device 64, monitor (not shown), processor (not shown) and electronic source (not shown). Among which, the resilient piece 61 is like a dome shape and is made of resilient, non-conductive material. In the center portion of the underside of the resilient piece 61 is the upper conductor 612. The base plate 62 is like a dome shape and is made of resilient non-conductive material. In the disk center are located the lower conductor 622. The separated lamina 63 is designed to include conductible material, so it can be conductive at a fixed on the spot where the resilient piece 61 and the base plate 62 are joined. There is a crevice between the separator board 63 and both the upper conductor 612 and the lower conductor 622. The sensor device 64 is fixed on the lower surface of the base plate 62, and is electrically-connected with the lower conductor 622. It is used to test the subject's physiological status and shows the results on the monitor. The processor is electrically connected to each of the following: upper conductor 612, the lower conductor 622, separated lamina 63 and sensor device 64, and is pre-installed with a deciding program. The contents of the program are as follows:

1. When the separated lamina 63 contacts first with the upper conductor 612, followed by the lower conductor 622, the sensor device 64 is activated, and starts to test; [0072] 2. When the separated lamina 63 contacts first with the lower conductor 622, followed by the upper conductor 612, no action is taken; [0073] 3. Under other circumstances, no action is taken without exception.

The electronic source provides the needed power to the sensor device 64, monitor and processor.

The electronic device 60 can be installed to the user's clothes. When the user lightly presses the resilient piece 61, it and the base plate 62 will change shape, causing the upper conductor 612 to come into contact first with the separated lamina 63, followed by the lower conductor 622. When the processor receives this information, it commands the sensor device 64 to start testing. On the contrary, when there is exaggerated movement from the user, causing the electronic device 60 to rub against the skin, there is an upward push from the skin, causing the lower conductor 622 to come into contact first with the separated lamina 63, followed by the upper conductor 612 contacted with the separated lamina 63. The processor will ignore this signal, thereby preventing the electronic device 30 to test by mistake.

Figure 13:
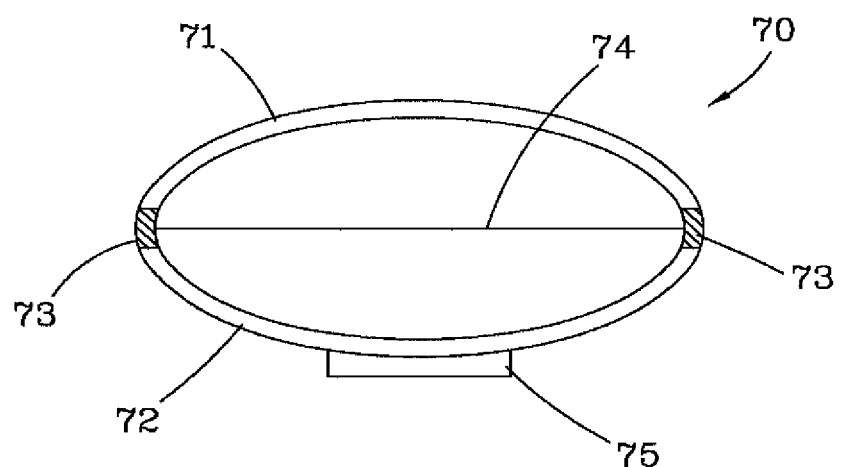
FIG. 13 shows a cut-away view of a seventh example embodiment of an electronic device of the present invention.

Comparing FIG. 13, this invention's seventh example embodiment of the electronic device 70 includes the upper conducting plate 71, the lower conducting plate 72, non-conductive material 73, separated lamina 74, sensor device 75, processor (not shown), output device (not shown), and a electronic source (not shown). Among which, the upper conducting plate 71 and the lower conducting plate 72 are dome-shaped, and are made of resilient, conductive material. The non-conductive material 73 forms ring-shaped, and the upper conducting plate 71 and lower conducting plate 72 are fixed to the upper and lower edges of the non-conductive material 73 respectively. The separated lamina 74 is located inside the non-conductive material 73, and is separated from the upper conducting plate 71 and lower conducting plate 72 by a crevice. The sensor device 75 is fixed on the lower surface of the lower conducting plate 72, and is electrically connected to the lower conducting plate 72. The sensor device is used to test the subject's physiological status. The processor is electrically connected to each of the following: upper conducting plate 71, the lower conducting plate 72, separated lamina 74 and sensor device 75, and is pre-installed with a deciding program. The contents of the program are as follows: [0077] 1. When the separated lamina 74 contacts first with the upper conducting plate 71, followed by the lower conducting plate 72, the sensor device 75 is activated, and starts to test; [0078] 2. When the separated lamina 74 contacts first with the lower conducting plate 72, followed by the upper conducting plate 71, no action is taken; [0079] 3. Under other circumstances, no action is taken without exception. The electronic source provides the needed power to the sensor device 75, monitor and processor.

Based on the above, this application example has the same effect as the sixth application example. If the user presses on the upper conducting plate 71, causing it to come into contact first with the separated lamina 74, followed by the lower conducting plate 72 coming into contact with the separated lamina 74, the processor will receive this signal and activate the sensor device 75 to start testing. On the contrary, if the signal comes first from the lower conducting plate 72 being pressed by mistake, the processor will ignore this signal. Hence, the electronic device 70 has both the advantageous features of testing at anytime and preventing testing by mistake.

A second aspect of the present invention is directed to a method of using the electronic device described in various interchangeable elements and embodiments above.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments that would come within the spirit and scope of the present invention.

Figure 14:
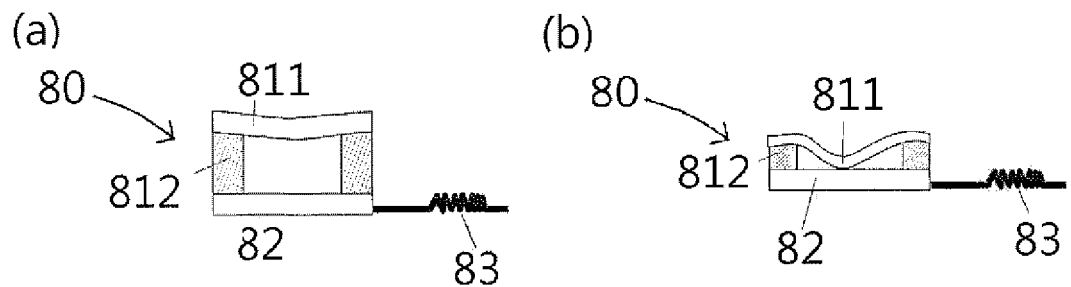
FIG. 14 shows a cut-away view of an eighth example embodiment of an electronic device of the present invention.

Moreover, there are several variations to this electronic device 10. As shown in FIG. 14, this invention's eighth example embodiment of the electronic device 80 includes a resilient piece 81, base plate 82, sensor device 83, monitor (not shown), and electronic source (not shown). Among which, the resilient piece 81 is made of upper conductor 811 such as a sliver textile and non-conductive resilient layer 812 such as rubber, foam-based material, spongy material, spring-liked material, cotton, spandex, lycra, synthetic rubber (SBR, Styrene Butadiene Rubber) and sponge-based material in order to increase its elasticity. The resilient piece 81 is also called the upper layer, whose non-conductive resilient layer 812 possesses a sufficient elasticity such that it will return to its original shape after being deformed. Base plate 82 is also called lower conductor or lower layer which can be formed in the following manners to have conductive material (but not limited to it):

1. By means of a textile process, weaving non-conductive fibers and conductive fibers together, either by knitting, weaving, tatting, embroidering or other appropriate means;

2. By embedding, sticking or sewing a conductive metallic plate, conductive rubber, or conductive silicon in the cloth material or non-conductive material layer;

3. By sewing fine, conductive wires into the cloth material or non-conductive material layer;

4. By applying a conductive material with adhesive substance over the cloth material or non-conductive material layer.

5. By sticking or sewing a conductive cloth material over the cloth material or non-conductive material layer.

The above-mentioned non-conductive textile fibers may be, but not limited to, cotton, hemp or nylon, while the conductive fibers may be polymer conductive fibers or conductive metallic fibers, or weaving a stainless steel fiber and a non-conductive fiber together, or applying a conductive substance over a non-conductive fiber. The percentage of the so-called conductive fibers is in the range between 1% and 100%.

There is a space between the upper conductor 811 and the lower conductor 82, such that the upper conductor 811 and the lower conductor 82 are not in contact until a force is applied to deform the upper layer 81. As shown in FIG. 14-a, it shows the normal condition without applied force, while FIG. 14-b shows the same object when force has been applied. In FIG. 14-b a force is applied on the resilient piece 81, causing non-conductive resilient 812 to be deformed. One of the examples of the sensor device 83 is a temperature sensor, which is electrically connected to the lower conductor 82. This sensor device 83 is used to test human body temperature, and shows the test results on the monitor. The advantage of the sensor device 83 not being located in the base plate 82 is that there is the same pressure distribution over upper layer 81 and base plate 82, there will not be an instance wherein there is an imbalance of pressure distribution. Hence, the closer the sensor device 83 is to the base layer 82, the better it is. The locations of the resilient piece 81 and the base plate 82 can be interchanged. And the electronic device can comprise a resilient piece joined between the sensor device and the lower layer to reduce the overlap space and perpendicular space, and also to achieve a shockproof and anti-interference effect.

The sensor device above, which connected with an upper conductor 811 or a lower layer 82, can also detect the breathing sounds, heart rhythm, EKG, body fat, sweat wetness, O2 saturation, pulse rate, blood pressure, body temperature, pressure, EMG, EEG, biochemical compounds, ultrasound, acceleration, rotation, tilt angle, urine sugar, heart sound, or lung sound, etc.

The electronic device further comprising at least one flexible blade, located between the upper layer and the lower layer, wherein at least one flexible blade has a fixed end located proximate to a joint between the upper layer and the lower layer and a free end located between the upper conductor and the lower conductor; wherein at least one flexible blade being made of a non-conductive material.

And the electronic device can comprise a separated lamina that is electrically conductive and fixed between the lower layer and the upper layer; and wherein a space is provided between the separated lamina and each of the upper conductor and the lower conductor.

One or more tape, ring, clothing or apparel attachment sites around a periphery of the electronic device for setting the electronic device on a piece of tape, a ring, a vehicle's steering wheel, or a piece of clothing or apparel.

The electronic device is used wherein a direction of the applied force defines an axis along which the sensor device and the lower layer are aligned.

The electronic device is disposed on an article to be worn or set or lied on or stood on or grasped, by a user to detect a user posture change.

Both of the electronic device and the sensor device are disposed on a keyboard or a cell-phone. For example, when user takes out the cell-phone or uses the keyboard, at the same time, we can receive the user's EKG or SPO2.

Otherwise, we can dispose the electronic device on the furniture such as a chair, a mattress, a toilet seat, etc. where people spend a lot of time on. So, it will be more comfortable and friendly for people to use in user's daily life.

As regards the sensor device for urine sugar, we can place the sensor device near a perineum of a diaper and the electrode device near the hip. So, when the user sits or lies down, we can receive the data from the sensor device we used.

Figure 15:
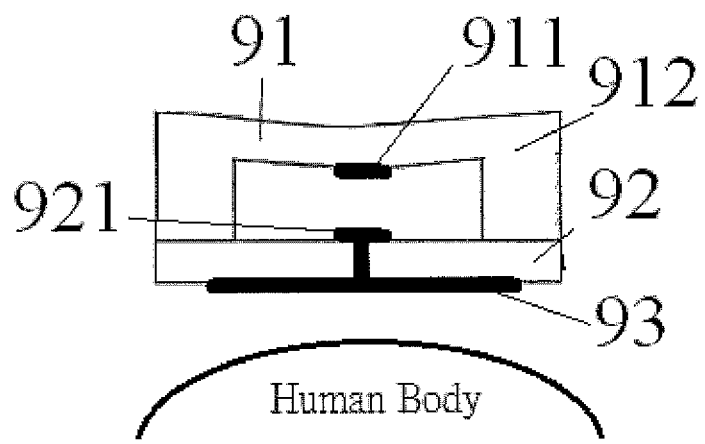
FIG. 15 shows a cut-away view of a ninth example embodiment of an electronic device of the present invention wherein a lower conductor is also as a part of the sensor.

There is another variation to this electronic device 10. As shown in FIG. 15, this invention's ninth example embodiment of the electronic device 90 includes a resilient piece 91, base plate 92, and sensor device 93. Among which, the resilient piece 91 is made of conductive material 911 such as a silver cloth and non-conductive resilient material 912 such as a sponge. The resilient piece 91 is also the upper layer. The so-called lower layer 92, is a non-conductive material. This lower layer 92 comprises a lower conductor 921 on the side facing the upper layer 912. The lower conductor 921 is also as a part of the sensor 93. There is a space between the lower conductor 921 and the upper conductor 911, such that the upper conductor 911 and the lower conductor 921 are not in contact until a force is applied to deform the upper layer. The applied force from the upper layer 91 to the lower layer 92 must be a balanced distribution, which shows that the upper conductor 911 and the lower conductor 921 are in contact when a pressure has been applied.

Figure 16:
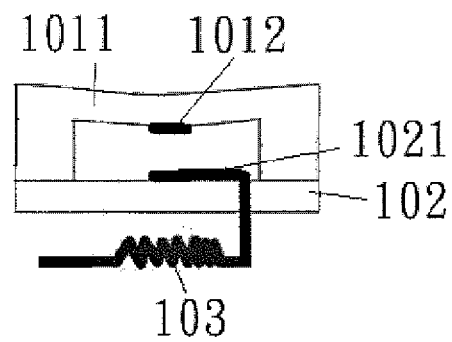
FIG. 16 shows a cut-away view of a tenth example embodiment of an electronic device of the present invention wherein a lower conductor is also as a part of the thermistor.

There is another variation to this electronic device 10. As shown in FIG. 16, this invention's ninth example embodiment of the electronic device 90, which is very similar to the electronic device 90 in FIG. 15, further includes a temperature sensor 103, one part of which is the lower conductor 1021. In other words, the lower conductor 1021 is made of one of the thermistor output pin. Among which, the resilient piece 101 is made of conductive material 1011 such as a steel plate and non-conductive resilient material 1012 such as a rubber. We can also replace the temperature sensor 103 to a microphone, galvanic skin response sensor, humidity sensor, pulse oxymeter, photo plethysmography sensor, blood pressure sensor, pressure sensor, biochemical compound sensor, ultrasonic sensor, accelerometer, gyroscope, lifter sensor, urine sugar sensor.

Figure 17:
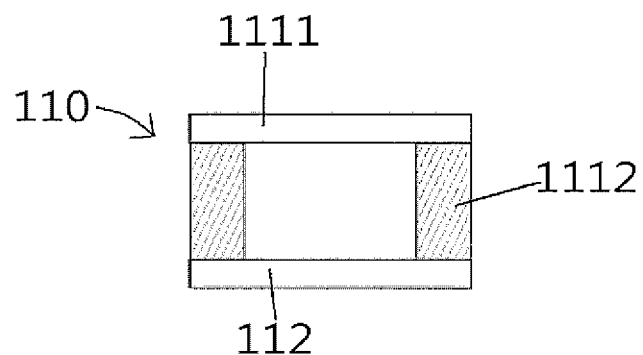
FIG. 17 shows a cut-away view of an eleventh example embodiment of an electronic device of the present invention wherein a lower conductor is also an electrode.

Moreover, there are several variations to this electronic device 10. As shown in FIG. 17, this invention's eleventh example embodiment of the electronic device 110 includes a resilient piece 111, base plate 112, sensor device 113, monitor (not shown), and electronic source (not shown). Among which, the resilient piece 111 is made of conductive material 1111 such as a silver cloth and non-conductive resilient material 1112 such as a spring.

The resilient piece 111 is also the upper layer. The base plate 112 is a conductive material that includes non-conductive material like conductive silicon rubber. It is also called lower layer 112. The part of the base plate 112 facing inward is to be used as a lower conductor, while that facing outward is used as an electrode. That is to say, the base plate 112 is a lower conductor and also an electrode at the same time. So, the applied force from the upper layer 111 to the lower layer 112 will be uniformly distributed, which shows that the upper conductor 1111 and the lower conductor 112 are in contact when a pressure has been applied. In another way, the base plate 112 is a cloth with silver coating on it. The inside face of the base plate 112 is to be used as a lower conductor, while that outside face of the base plate is non-conductive. Now the lower conductor is also used as a capacitive electrode, so the lower conductor is a sensor device too. The electrode can be used to detect ECG, EEG, EMG, etc. It also can be used for TENS or electric shock. The resilient piece 111 is also can be used as an electrode, too.

Figure 18:
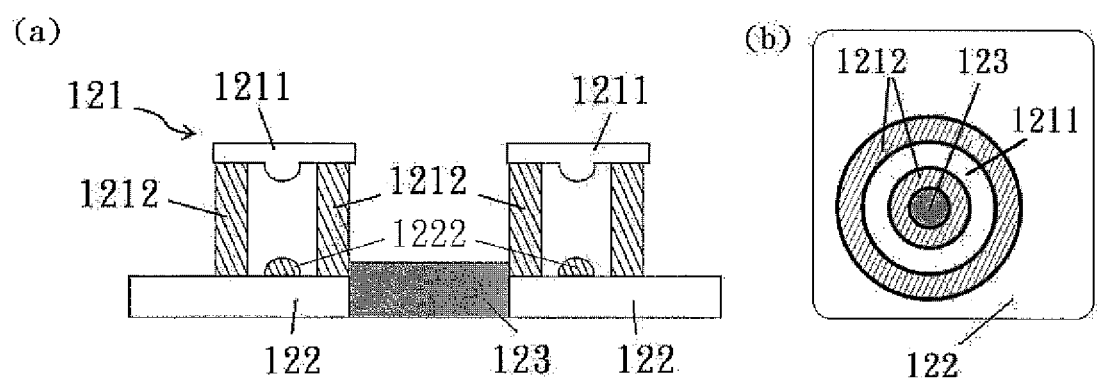
FIG. 18 shows a cut-away view of a twelfth example embodiment of an electronic device of the present invention wherein the sensor device located in the lower layer.

There is another variation to this electronic device 10. As shown in FIG. 18, this invention's twelfth example embodiment of the electronic device 120 includes a resilient piece 121, base plate 122, and sensor device 123. Among which, the resilient piece 121 is made of conductive material 1211 such as a cloth made of conductive fiber, and non-conductive resilient material 1212 such as a foam-based material.

The resilient piece 121 is also the upper layer. The non-conductive resilient material 1212 possess a sufficient elasticity such that it will return to its original shape after being deformed. The base plate 122 includes lower conductor 1222. There is a space between the upper conductor 1211 and the lower conductor 1222, such that the upper conductor 1211 and the lower conductor 1222 are not in contact until a force is applied to deform the upper layer. The sensor device 123 located in the center of the electronic device and electrically connected to the lower conductor 1222. The electronic source provides the needed power to the sensor device 123 and the monitor. FIG. 18-a, shows the cut-away view of the electronic device 120 in its normal condition without an applied force. And FIG. 18-b shows the top view of the same object. The sensor device 123 is placed in the center of the electronic device 120 to reduce the overlap space and perpendicular space, and also to achieve a shockproof and anti-interference effect. The applied force from the upper layer 1211 to the lower layer 122 will be a uniformly distributed, which shows that the upper conductor 1211 and the lower conductor 1222 are in contact when a pressure has been applied. This electronic device is hollow and symmetrical, and the shape of the electronic device can be a circle, square, oblong, rectangle, and so on. The sensor device 123 is placed in the hollow of the electronic device, for example, the sensor in FIG. 18 can be a microphone or ultrasound, etc.

Figure 19:
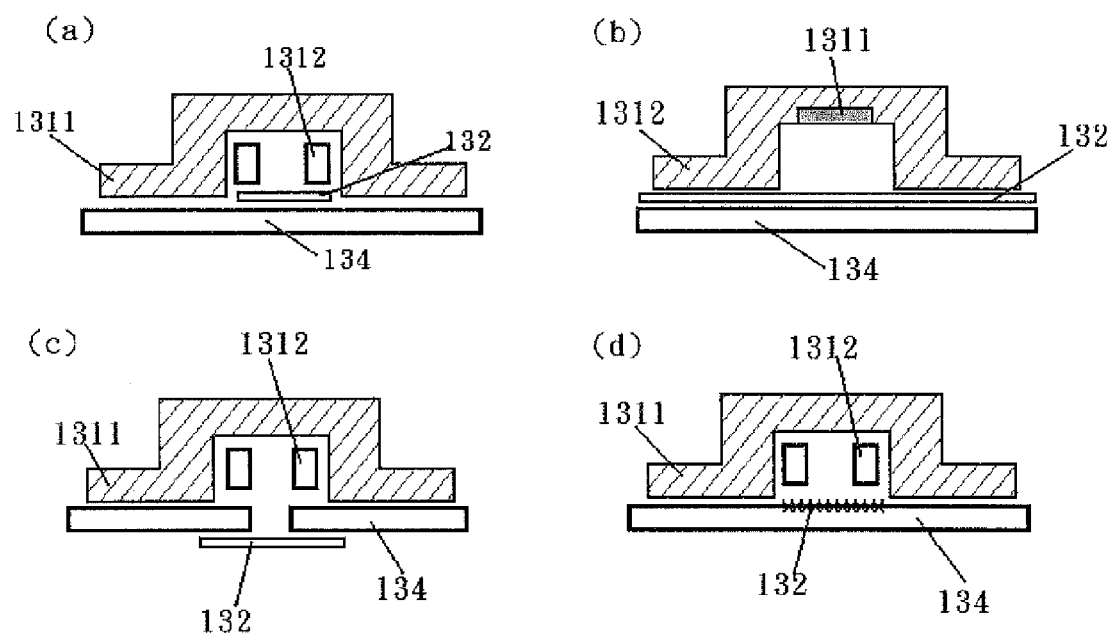
FIG. 19 shows the cut-away view of four different configurations of an electronic device affixed to cloth.

As shown in FIG. 19, those electronic devices show above can be fixed on garment or a piece of cloth into four different configurations. The electronic device further comprising a garment or a piece of cloth to which the lower layer or upper layer is affixed. The affixed method can place the electronic device between fibers of the piece of the cloth or the garment.

In FIG. 19-(a), the first configuration includes a resilient piece 131, base plate 132, sensor device 133 (not shown), and garment or a piece of cloth 134. The resilient piece 131 is also an upper layer; and the base plate 132 is a conductive textile, so it also acts as the lower conductor. The resilient piece 131 made of conductive material 1311 such as a conductive textile and non-conductive resilient material 1312 such as a sponge. The conductive material 1311 is also an upper conductor. Both of the conductive material 1311 and lower layers 132 are sewn on the same side of the garment 134. There is a space between the lower conductor 132 and the upper conductor 1311, such that the upper conductor 1311 and the lower conductor 132 are not in contact until a force is applied to deform the non-conductive resilient material 1312.

FIG. 19-(b) is similar to FIG. 19-(a). But its conductive material 1311, in FIG. 19-(b), is located on the central portion of the lower surface of the non-conductive resilient material 1312 such as rubber. There is a space between the lower conductor 132 and the upper conductor 1311. Both of the upper and lower layers are on the same side of the garment 134: the non-conductive resilient material 1312 is fixed to the lower layer 132 and the lower layer 132 is fixed to the subject's garment 134, such that the upper conductor 1311 and the lower conductor 132 are not in contact until a force is applied to deform the upper layer.

FIG. 19-(c) is similar to FIG. 19-(a). The only difference between them is the upper layer 131 and lower layer 132 are at the opposite side of the garment 134. There is a gap on the garment 134 between the upper layer 131 and lower layer 132, so the piece of cloth 134 is fixed between upper layer 131 and lower layer 132.

FIG. 19-(d) is similar to FIG. 19-(a) the only difference between them is the lower layer 132 is combined with the garment or a piece of cloth 134 which can be formed in the following manners to have conductive material (but not limited to it):

1. By means of a textile process, weaving non-conductive fibers and conductive fibers together, either by knitting, weaving, tatting, embroidering or other appropriate means;
2. By embedding, sticking or sewing a conductive metallic plate, conductive rubber, or conductive silicon in the cloth material or non-conductive material layer;
3. By sewing fine, conductive wires into the cloth material or non-conductive material layer;
4, By applying a conductive material with adhesive substance over the cloth material or non-conductive material layer.
5. By sticking or sewing a conductive cloth material over the cloth material or non-conductive material layer.

The electronic device is disposed on a garment or an article to be worn, sat on, or lied on by a user to detect a user posture change. For example, we set four electrode devices on a shirt on its anterior, bilateral, and posterior sides. When the user lies on the bed, we can receive the data from the electrode device we used.

The sensor device in these four configurations above can be used as an electrode. Otherwise the sensor device can be affixed in the garment or a piece of cloth by knitting, weaving, tatting, embroidering or other appropriate means, and the sensor device is connected with the electronic device, either upper conductor or lower conductor.

Figure 20:
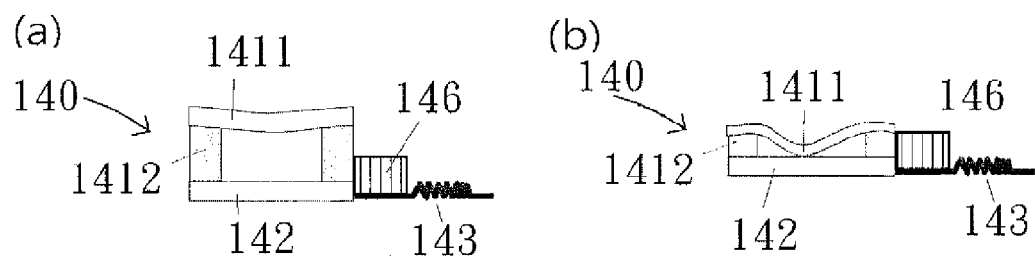
FIG. 20 shows a cut-away view of a thirteenth example embodiment of an electronic device of the present invention wherein a resilient piece or an elastic piece placed between a lower conductor and a sensor device.

There is another variation to this electronic device 10. As shown in FIG. 20, this invention's thirteenth example embodiment of the electronic device 140 is very similar to the electronic device 80 in FIG. 14. The only distinct from the electronic device 80 is the electronic device 140 placed a resilient or elastic piece 146 between the lower layer 142 and the sensor device 143. The resilient or elastic piece 146 possess a sufficient elasticity or resilience such that it will return to its original shape after being pressed, pulled, or stretched. For example, a steel plate can be resilience, a piece of conductive silicon rubber can be resilience or elasticity, and elastic conductive fiber can be elasticity, etc. The advantage of installing the resilient or elastic piece 146 is to achieve a stretch-proof, shockproof, and anti-interference effect for the sensor device 143. When the sensor device 143 is used to detect the user's vital sign the resilient or elastic piece 146 can reduce the noise during applied force deformed this electronic device 140.

Figure 21:
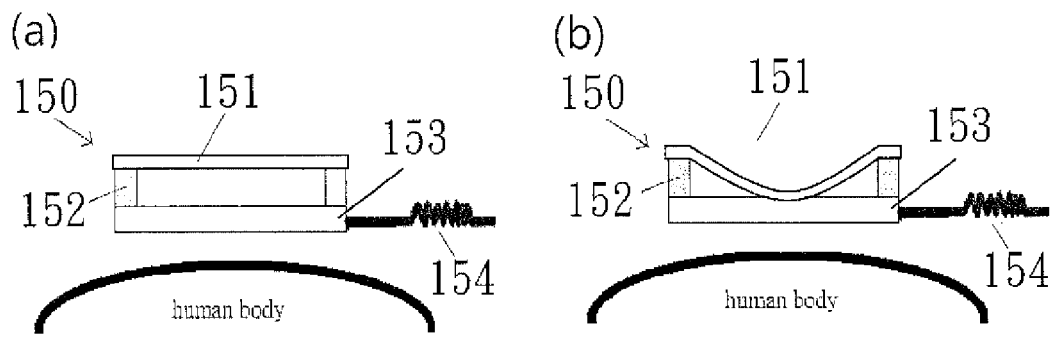
FIG. 21 shows a cut-away view of a fourteenth example embodiment of an electronic device of the present invention.

Moreover, there is another variation to this electronic device 30. As shown in FIG. 21, this invention's fourteenth example embodiment of the electronic device 150 includes an upper conductor 151, a non-conductive intermediate layer 152, lower conductor 153, and a sensor device 154. Among which, one of the upper conductor 151 and the lower conductor 153, is made of resilient conductive material or elastic material, possess a sufficient resilience or elasticity such that it will return to its original shape after being pressed, pulled, or stretched, for example, a steel plate can be resilience, a piece of conductive silicon rubber can be resilience or elasticity, and elastic conductive fiber can be elasticity, etc. The upper conductor 151 and lower conductor 153 are separated from the non-conductive intermediate layer 152 to form a space, such that the upper conductor 151 and the lower conductor 153 are not in contact until a force is applied to deform the upper layer 151. As shown in FIG. 21-a, it shows the normal condition without applied force, while FIG. 21-b shows the same object when force has been applied. In FIG. 21-b the subject applied pressure on the upper conductor 151 causing it to be deformed. The applied example of the sensor device 154 is a temperature sensor, which is electrically connected to the lower conductor 153. This sensor device 154 is used to test human body temperature, and shows the test results on the monitor. The electronic source provides the needed power to the sensor device 154 and the monitor. The advantage of the sensor device 154 not being located in the lower conductor 153 is that there is the same pressure distribution over upper conductor 151 and lower conductor 153, there will not be an instance wherein there is an imbalance of pressure distribution. Hence, the closer the sensor device 154 is to the lower conductor 153, the better it is. The locations of the upper conductor 151 and the lower conductor 153 can be interchanged. And the electronic device can comprise a resilient piece joined between the sensor device and the lower layer to reduce the overlap space and perpendicular space, and also to achieve a shockproof and anti-interference effect.

There is another variation to this electronic device 30. This invention's another example embodiment of the electronic device, which is very similar to the electronic device 90 in FIG. 15, includes an upper conductor which is made of resilient conductive material or elastic material, a non-conductive intermediate layer, lower conductor, and a sensor device. The upper conductor can be a steel plate, a piece of conductive silicon rubber or elastic conductive fiber, etc. The upper conductor and lower conductor are separated from the non-conductive intermediate layer to form a space, such that the upper conductor and the lower conductor are not in contact until a force is applied to deform the upper layer. The lower conductor is also as a part of the sensor device. The sensor device can be a temperature sensor, and one part of it is the lower conductor. In other words, the lower conductor is made of one of the thermistor output pin. We can also replace the temperature sensor to a microphone, galvanic skin response sensor, humidity sensor, pulse oxymeter, photo plethysmography sensor, blood pressure sensor, pressure sensor, biochemical compound sensor, ultrasonic sensor, accelerometer, gyroscope, tilter sensor, urine sugar sensor.

We also can design an electronic device as in FIG. 17, but the lower conductor or upper layer is used as an electrode, i.e. lower conductor or upper layer is sensor device, too.

Figure 22:
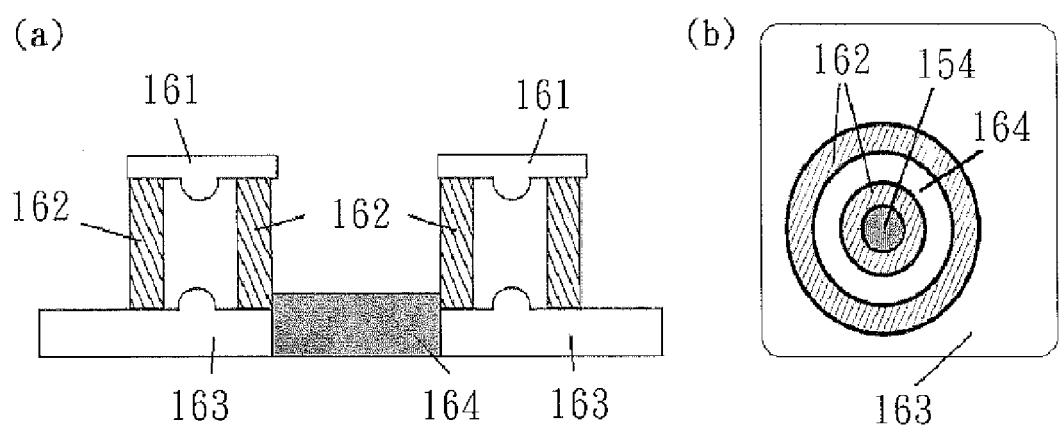
FIG. 22 shows a cut-away view of a fifteenth example embodiment of an electronic device of the present invention wherein the sensor device located in the lower layer.

There is another variation to this electronic device 30. As shown in FIG. 22, this invention's fifteenth example embodiment of the electronic device 160 includes an upper conductor 161, a non-conductive intermediate layer 162, a lower conductor 163, a sensor device 164. FIG. 22-*a*, shows the cutaway view of the electronic device in its normal condition without an applied force. And FIG. 22-*b* shows the top view of the same object. The upper conductor 161 and the lower conductor 163 are not in contact until a force is applied to deform the upper conductor 161. The sensor device 164 is placed in the center of the electronic device to reduce the overlap space and perpendicular space, and also to achieve a shockproof and anti-interference effect.

We also can design this structure to fix on garment or a piece of cloth into four different configurations. The first configuration includes an upper conductor, a non-conductive intermediate layer, a lower conductor, a sensor device (not shown), and a garment or a piece of cloth. Both the upper conductor and lower conductor are sewn on the same side of the garment. There is a space between the upper conductor and lower conductor, such that the upper conductor and the lower conductor are not in contact until a force is applied to deform the upper conductor. At the same time, the non-conductive intermediate layer is not deformed by the applied force.

The second configuration is similar to the first one, but its upper conductor is located on the central portion of the lower surface of the non-conductive intermediate layer. There is a space between the upper conductor and the lower conductor. Both the upper and lower conductors are on the same side of the garment: the non-conductive intermediate layer is fixed to the lower conductor and the lower conductor is fixed to the garment, such that the upper conductor and the lower conductor are not in contact until a force is applied to deform the lower conductor.

The third configuration is similar to the first one. The only difference between them is the upper conductor and lower conductor are on opposite sides of the garment. There is a gap on the garment between the upper conductor and lower conductor, so the piece of cloth is fixed between upper and lower conductors.

The last configuration is similar to the first one. The only difference between them is the lower conductor is combined with the garment or a piece of cloth which can be formed in the following manners to have conductive material (but not limited to it):

1. By means of a textile process, weaving non-conductive fibers and conductive fibers together, either by knitting, weaving, tatting, embroidering or other appropriate means;

2. By embedding, sticking or sewing a conductive metallic plate, conductive rubber, or conductive silicon in the cloth material or non-conductive material layer;

3. By sewing fine, conductive wires into the cloth material or non-conductive material layer;

4. By applying a conductive material with adhesive substance over the cloth material or non-conductive material layer.

5. By sticking or sewing a conductive cloth material over the cloth material or non-conductive material layer.

Figure 23:
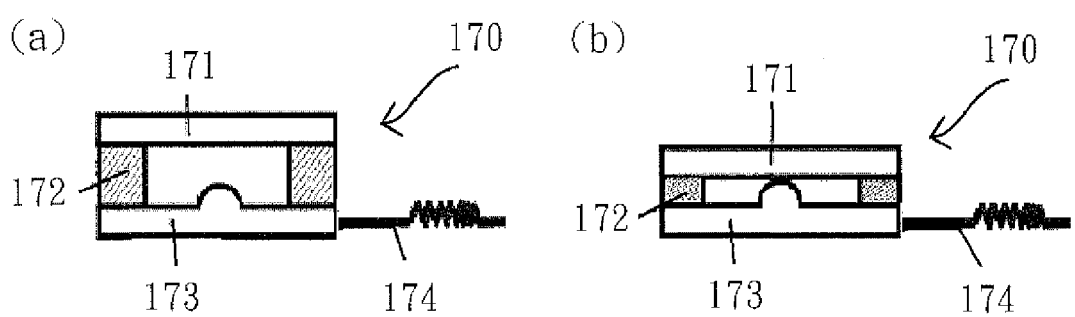
FIG. 23 shows a cut-away view of a sixteenth example embodiment of an electronic device of the present invention.

Moreover, there is a new variation to this electronic device 170. As shown in FIG. 23, this invention's sixteenth example embodiment of the electronic device includes an upper conductor 171, a non-conductive intermediate resilient layer 172, a lower conductor 173, a sensor device 174, monitor (not shown), and electronic source (not shown). The non-conductive intermediate resilient layer 172, possessed a sufficient elasticity such that it will return to its original shape after being deformed, can be rubber, foam-based material, spongy material, spring-liked material, cotton, spandex, lycra, synthetic rubber (SBR, Styrene Butadiene Rubber) and sponge-based material in order to increase its elasticity.

There is a space between the upper conductor 171 and the lower conductor 173, such that the upper conductor 171 and the lower conductor 173 are not in contact until a force is applied to deform the non-conductive intermediate resilient layer 172. As shown in FIG. 23-*a*, it shows the normal condition without applied force, while FIG. 23-*b* shows the same object when force has been applied. In FIG. 23-*b* the subject applied pressure on the upper conductor 171, causing the non-conductive intermediate resilient layer 172 to be deformed. The applied example of the sensor device 174 is a temperature sensor, which is electrically connected to the lower conductor 173. This sensor device 174 is used to test human body temperature, and shows the test results on the monitor. The electronic source provides the needed power to the sensor device 174 and the monitor. The advantage of the sensor device 174 not being located in the lower conductor 173 is that there is the same pressure distribution over upper conductor 171 and lower conductor 173, there will not be an instance wherein there is an imbalance of pressure distribution. Hence, the closer the sensor device 174 is to the lower conductor 173, the better it is. And the electronic device can comprise a resilient piece joined between the sensor device and the lower layer to reduce the overlap space and perpendicular space, and also to achieve a shockproof and anti-interference effect.

There is a new variation to this electronic device 170. This invention's another example embodiment of the electronic device, which is very similar to the electronic device 90 in FIG. 15, includes an upper conductor, a non-conductive intermediate resilient layer, a lower conductor, a sensor device, monitor, and electronic source. The non-conductive intermediate resilient layer, possessed a sufficient elasticity such that it will return to its original shape after being deformed, can be rubber, foam-based material, spongy material, spring-liked material, cotton, spandex, lycra, synthetic rubber (SBR, Styrene Butadiene Rubber) and sponge-based material in order to increase its elasticity. The upper conductor and lower conductor are separated from the non-conductive intermediate resilient layer to form a space, such that the upper conductor and the lower conductor are not in contact until a force is applied to deform the non-conductive intermediate resilient layer. The lower conductor is also as a part of the sensor device. The sensor device can be a temperature sensor, and one part of it is the lower conductor. In the other words, the lower conductor is made of one of the thermistor output pin.

We also can design an electronic device as in FIG. 17, but the lower conductor or upper layer is to used as an electrode, i.e. lower conductor or upper layer is a sensor device, too.

There is a new variation to this electronic device 170, which is very similar to the electronic device 160 in FIG. 22, includes an upper conductor, a non-conductive intermediate layer, a lower conductor, sensor device, monitor, and electronic source. And the non-conductive intermediate layer possessed sufficient elasticity such that it will return to its original shape after being deformed, can be rubber, foam-based material, spongy material, spring-liked material, cotton, spandex, lycra, synthetic rubber (SBR, Styrene Butadiene Rubber) and sponge-based material in order to increase its elasticity.

The non-conductive intermediate resilient layer possesses a sufficient elasticity such that the upper conductor and the lower conductor are not in contact until a force is applied to deform the non-conductive intermediate resilient layer.

FIG. 22-a, shows the cut-away view of the electronic device in its normal condition without an applied force. And FIG. 22-b shows the top view of the same object. The sensor device is placed in the center of the electronic device to reduce the overlap space and perpendicular space, and also to achieve a shockproof and anti-interference effect.

This electronic device is hollow and symmetrical, and the shape of the electronic device can be a circle, square, oblong, rectangle, and so on. The sensor device is placed in the hollow of the electronic device, for example, the sensor in FIG. 22 can be a microphone or ultrasound, etc.

We also can design this structure to be fixed on garment or a piece of cloth into four different configurations.

The first configuration includes an upper conductor, non-conductive intermediate resilient layer, a lower conductor, a sensor device (not shown), and a garment or a piece of cloth. Both the upper conductor and lower conductor are sewn on the same side of the garment. There is a space between the upper conductor and lower conductor, such that the upper conductor and the lower conductor are not in contact until a force is applied to deform the non-conductive intermediate resilient layer.

The second configuration is similar to the first one, but its upper conductor is located on the central portion of the lower surface of the non-conductive intermediate resilient layer. There is a space between the upper conductor and the lower conductor. Both of the upper and lower conductors are on the same side of the garment: the non-conductive intermediate resilient layer is fixed to the lower conductor and the lower conductor is fixed to the garment, such that the upper conductor and the lower conductor are not in contact until a force is applied to deform the non-conductive intermediate resilient layer.

The third configuration is similar to the first one. The only difference between them is the upper conductor and the lower conductor are on opposite sides of the garment. There is a gap on the garment between the upper conductor and lower conductor, so the piece of cloth is fixed between upper and lower conductors.

The last configuration is similar to the first one. The only difference between them is the lower conductor is combined with the garment or a piece of cloth which can be formed in the following manners to have conductive material (but not limited to it):

1. By means of a textile process, weaving non-conductive fibers and conductive fibers together, either by knitting, weaving, tatting, embroidering or other appropriate means;

2. By embedding, sticking or sewing a conductive metallic plate, conductive rubber, or conductive silicon in the cloth material or non-conductive material layer;

3. By sewing fine, conductive wires into the cloth material or non-conductive material layer;

4. By applying a conductive material with adhesive substance over the cloth material or non-conductive material layer.

5. By sticking or sewing a conductive cloth material over the cloth material or non-conductive material layer.

What is claimed is:

1. An electronic device comprising: an upper layer made of a non-conductive material; a lower layer made of a non-conductive material; wherein at least one of the upper layer and the lower layer is made of a resilient material having a sufficient elasticity such that it will return to an original shape after being deformed, wherein the upper layer comprises an upper conductor and the lower layer comprises a lower conductor and a space is provided between the upper conductor and the lower conductor such that the upper conductor and the lower conductor are not in contact until a force is applied to deform at least one of the upper layer and the lower layer; and a sensor device for human body testing connected with the lower conductor, or the lower conductor is configured to function as part of a sensor device for human body testing.

2. The electronic device of claim 1, wherein a lower conductor functions as part of the sensor device.

3. The electronic device of claim 2, wherein the sensor device is a thermistor, microphone, galvanic skin response sensor, humidity sensor, pulse oxymeter, photo plethysmography sensor, blood pressure sensor, pressure sensor, biochemical compound sensor, ultrasonic sensor, accelerometer, gyroscope, tilter sensor, urine sugar sensor.

4. The electronic device of claim 2, wherein the sensor device is an electrode and the lower layer functions as part of the electrode.

5. The electronic device of claim 1, wherein the sensor device is located on the lower layer or the upper layer.

6. The electronic device of claim 1, wherein the sensor device is located in the lower layer.

7. The electronic device of claim 1, further comprising a garment or a piece of cloth to which the lower layer or the upper layer is affixed.

8. The electronic device of claim 7, wherein the piece of cloth is placed between the upper layer and the lower layer.

9. The electronic device of claim 7, wherein the electronic device is placed between fibers of the piece of cloth or the garment.

10. The electronic device of claim 7, the lower conductor or the upper conductor functions as an electrode.

11. The electronic device of claim 1 wherein the upper layer and the lower are made of the resilient material have varying thicknesses or different moduli of elasticity to provide a desired sensitivity of the electronic device.

12. The electronic device of claim 1 wherein the upper layer and the lower layer are both resilient.

13. The electronic device of claim 1 wherein the sensor device is capable of detecting breathing sounds, heart rhythm, EKG, body fat, sweat wetness, O2 saturation, pulse rate, blood pressure, body temperature, pressure, EMG, EEG, biochemical compounds, ultrasound, acceleration, rotation, tilt angle, urine sugar, heart sound, or lung sound.

14. The electronic device of claim 1, further comprising a resilient piece joined between the sensor device and the lower layer.

15. The electronic device of claim 1, further comprising at least one flexible blade located between the upper layer and the lower layer, wherein the at least one flexible blade has a fixed end located proximate to a joint between the upper layer and the lower layer and a free end located between the upper conductor and the lower conductor, wherein the at least one flexible blade being made of a non-conductive material.

16. The electronic device of claim 1, further comprising a separated lamina that is electrically conductive and fixed between the lower layer and the upper layer, and wherein a space is provided between the separated lamina and each of the upper conductor and the lower conductor.

17. The electronic device of claim 1 wherein a sensor device electrically connects to a processor that is equipped with functions to turn the sensor device on and off, and to change a sensing time, a sensing frequency, or a sensing mode of the sensor device.

\* \* \* \* \*